United States Patent
Olmstead

(10) Patent No.: US 9,931,381 B2
(45) Date of Patent: *Apr. 3, 2018

(54) METHODS OF COMPRISING SERRATIA PEPTIDASE FOR INHIBITION AND TREATMENT OF BIOFILMS RELATED TO CERTAIN CONDITIONS

(75) Inventor: Stephen Francis Olmstead, Reno, NV (US)

(73) Assignee: PROTHERA, INC., Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,775

(22) Filed: Nov. 23, 2010

(65) Prior Publication Data

US 2011/0129454 A1    Jun. 2, 2011

Related U.S. Application Data

(60) Provisional application No. 61/263,776, filed on Nov. 23, 2009.

(51) Int. Cl.
| | | |
|---|---|---|
| A61K 38/54 | (2006.01) | |
| A61K 38/48 | (2006.01) | |
| A61K 38/46 | (2006.01) | |
| A61K 38/47 | (2006.01) | |
| A61K 9/00 | (2006.01) | |
| A61K 38/40 | (2006.01) | |
| A61K 36/82 | (2006.01) | |
| A61K 31/352 | (2006.01) | |

(52) U.S. Cl.
CPC ............ *A61K 38/47* (2013.01); *A61K 9/0034* (2013.01); *A61K 9/0043* (2013.01); *A61K 9/0046* (2013.01); *A61K 31/352* (2013.01); *A61K 36/82* (2013.01); *A61K 38/40* (2013.01); *A61K 38/482* (2013.01); *A61K 38/4873* (2013.01); *A61K 38/4886* (2013.01)

(58) Field of Classification Search
CPC ...... A61K 38/54; A61K 38/48; A61K 38/482; A61K 38/4833; A61K 38/46; A61P 71/00
USPC ...................... 424/94.2, 94.63, 94.64, 94.65
See application file for complete search history.

(56) References Cited

U.S. PATENT DOCUMENTS

| | | | |
|---|---|---|---|
| 6,830,745 B1 * | 12/2004 | Budny et al. .................... | 424/49 |
| 7,060,674 B2 | 6/2006 | Lim et al. | |
| 7,229,809 B2 | 6/2007 | Veronesi et al. | |
| 2003/0206875 A1 * | 11/2003 | Budny ...................... | A61K 8/64 424/49 |
| 2006/0121019 A1 * | 6/2006 | Budny et al. ............. | 424/94.61 |
| 2006/0140881 A1 * | 6/2006 | Xu et al. .......................... | 424/49 |
| 2008/0139545 A1 * | 6/2008 | Choe ................... | A61K 31/5383 514/230.2 |

OTHER PUBLICATIONS

Swidsinski et al. Adherent Biofilms in Bacterial Vaginosis; Obstetrics and Gynecology, vol. 106, Pt. 1 (2005) pp. 1013-1023 (abstract only).*

Brady et al. Osteomyelitis and the Role of Biofilms in Chronic Infection; FEMS Immunology and Medical Microbiology, vol. 52 (2008) pp. 13-22.*

Prince et al. Prevalence of Biofilm-Forming Bacteria in Chronic Rhinosinusitis; American Journal of Rhinology, vol. 22, No. 3 (2008) pp. 239-245 (abstract only).*

Dongari-Bagtzoglou, A. Pathogenesis of Mucosal Biofilm Infections: Challenges and Progress; Expert Review of Anti-Infective Therapy, vol. 6, No. 2 (2008) pp. 201-208.*

MacFarlane et al. Microbial Biofilms in the Human Intestinal Tract; Journal of Applied Microbiology, vol. 102 (2007) pp. 1187-1196.*

Parkes et al. Gastrointestinal Microbiota in Irritable Bowel Syndrome: Their Role in Its Pathogenesis and Treatment; American Journal of Gastroenterology, vol. 103 (2008) pp. 1557-1567.*

Longhi et al. Protease Treatment Affects Both Invasion Ability and Biofilm Formation in Listeria Monocytogenes; Microbial Pathogenesis, vol. 45 (2008) pp. 45-52.*

Cohen, P. Dissolve Biofilms With Fibrinolytic Enzymes: A Novel Approach to Chronic Infection in Autism Spectrum Disorders; Nutricology Newsletter, Mar. 2009, pp. 11-12. downloaded from http://www.nutricology.com/infocus/pdfletters/InFocus_2009Mar_Earthworms.pdf on Nov. 28, 2012.*

Selan et al. Proteolytic Enzymes: A New Treatment Strategy for Prosthetic Infections; Antimicrobial Agents and Chemotherapy, vol. 37, No. 12 (1993) pp. 2618-2621.*

Trampuz et al. Infections Associated With Orthopedic Implants; Current Opinion in Infectious Diseases, vol. 19 (2006) pp. 349-356.*

Harvey et al. Biofilms and Chronic Rhinosinusitis: Systemic Review of Evidence, Current Concepts and Directions for Research; Rhinology, vol. 45 (2007) pp. 3-13.*

Braun et al. Therapeutic Use, Efficiency and Safety of the Proteolytic Pineapple Enzyme Bromelain-POS in Children With Acute Sinusitis in Germany; In Vivo, vol. 19 (2005) pp. 417-422.*

Cohen, P. Dissolve Biofilms With Fibrinolytic Enzymes: A Novel Approach to Chronic Infection in Autism Spectrum Disorders; Nutricology Newsletter, Mar. 2009, pp. 11-12. downloaded from http://www.nutricology.com/infocus/pdfletters/InFocus_2009Mar_Earthworms.pdf on May 15, 2014.*

Moriya et al. Intestinal Absorption of Serrapeptase (TSP) in Rats; Biotechnology and Applied Biochemistry, vol. 20 (1994) pp. 101-108.*

(Continued)

*Primary Examiner* — Scott Long
*Assistant Examiner* — Paul Martin
(74) *Attorney, Agent, or Firm* — Isaac Angres

(57) ABSTRACT

Physiologically acceptable anti-biofilm compositions comprising *Serratia* peptidase and optionally one or more of bromelain, papain and a fibrinolytic enzyme. Additional components can include antimicrobials, antibiotics, antifungals, herbals, chelating agents, lactoferrin and related compounds, minerals, surfactants, binders, and fillers useful for the inhibition and treatment of gastrointestinal biofilms in humans. Physiologically acceptable anti-biofilm compositions containing these enzymes are useful in the inhibition, reduction and/or treatment of biofilms such as in the ear, vagina, joints, bones, gut, surgical sites and other locations, and are useful for the inhibition, reduction and/or treatment of associated systemic symptoms caused by biofilm associated microorganisms.

9 Claims, No Drawings

(56) References Cited

OTHER PUBLICATIONS

Olmstead et al. Life on the Edge: The Clinical Implications of Gastrointestinal Biofilm; Townsend Letter, Oct 1, 2009. pp. 1-12, downloaded from http://www.thefreelibrary.com//printArticle.aspx?id=211561662 on May 15, 2014.*

Rawat et al. An Overview of Miracle Enzyme-Serratiapeptidase; Research Journal of Pharmacy and Technology, vol. 1, No. 3 (Jul.-Sep. 2008). pp. 124-131.*

Roveta et al. Activity of Moxifloxacin on Biofilms Produced In Vitro by Bacterial Pathogens Involved in Acute Exacerbations of Chronicbronchitis; International Journal of Antimicrobial Agents, vol. 30 (2007) pp. 415-421.*

Nakamura et al. Effect of the Proteolytic Enzyme Serrapeptase in Patients With Chronic Airway Disease; Respirology, vol. 8 (2003) pp. 316-320.*

Anonymous, USANA Tehcnical Bulletin (2008) pp. 1-2. downloaded from https://www.usana.com/media/file/dotCom/company/science/components/Bromelain.pdf on Oct. 28, 2014.*

Mazzone et al. Evaluation of Serratia Peptidase in Acute or Chronic Inflammation of Otorhinolaryngology Pathology: A Multicentre, Double-Blind, Randomized Trial Versus Placebo; The Journal of International Medical Research, vol. 18 (1990) pp. 379-388.*

Shahid et al. Efficacy and Safety of Phlogenzym-A Protease Formulation, in Sepsis in Children; Journa of the Association of Physicians of India, vol. 50 (2002) pp. 527-531 (Abstract only).*

Vlastarakos et al. Biofilms in Ear, Nose and Throat Infections: How Important are They?; The Laryngoscope, vol. 117 (2007) pp. 668-673.*

Veldova et al. Use of Phlogenzym in the Treatment of Secretory Otitis in the Outpatient Practice; Congress of the Czech Society of Otorhinolaryngology and Surgery of Head and Neck, Sep. 9-11, 1999 downloaded from www.enzymestuff.com/conditionbacteriaresearch.htm on Jun. 22, 2015.*

Wakabayashi et al. Inhibitory Effects of Lactoferrin on Growth and Biofilm Formation of Porphyromonas Gingivalis and Prevotella Intermedia; Antimicrobial Agents and Chemotherapy, vol. 53, No. 8 (May 18, 2009) pp. 3308-3316.*

Takeuchi et al. Enteric-Formulated Lactoferrin Was More Effectively Transported Into Blood Circulation From Gastrointestinal Tract in Adult Rats; Experimental Physiology, vol. 91, No. 6 (2006) pp. 1033-1040.*

Singh et al. A Component of Innate Immunity Prevents Bacterial Biofilm Development; nATURE, vol. 417 (2002) pp. 552-555.* wikipedia.org, Definition of "biofilm" [retrieved on Dec. 21, 2010]. Retrieved from the Internet: < URL: http://en.wikipedia.org/wiki/Biofilm>, pp. 1-10.

Donlan et al. (2002) "Biofilms: Survival Mechanisms of Clinically Relevant Microorganisms"; Clin. Microbiol. Rev.; 15167-293.

Potera (1999) "Forging a Link Between Biofilms and Disease"; Science; 283:1837-8.

Veldova et al. Use of Phlogenzym in the Treatment of Secretory Otitis in the Outpatient Practice; Congress of the Czech Society of Otorhinolaryngology and Surgery of Head and Neck, Sep. 9-11, 1999 downloaded from www.enzymestuff.com/conditionbacteriaresearch.htm on Jun. 22, 2015.

Donlan (2001) "Biofilms and Device-Associated Infections"; Emerg. Infect. Dis.; 7:277-81.

Donskey (2004) "The Role of the Intestinal Tract as a Reservoir and Source for Transmission of Nosocomial Pathogens"; Clin. Infect. Dis.; 39:219-26.

MacFarlane et al. (2006) "Composition and Metabolic Activities of Bacterial Biofilms Colonizing Food Residues in the Gastrointestinal Tract"; Appl. Environ. Microbiol.; 72:6204-11.

Probert et al. (2002) "Bacterial Biofilms in the Human Gastrointestinal Tract"; Curr: Issues Intest. Microbiol.; 3:23-7.

Itoh et al. (2005) "Depolymerization of $\beta$-1,6-N-Acetyl-D-Glucosamine Disrupts the Integrity of Diverse Bacterial Biofilms"; J. Bacteriol.; 187:382-7.

Kaplan et al. (2003) "Detachment of Actinobacillus Actinomycetemcomitans Biofilm Cells by an Endogenous $\beta$-Hexosaminidase Activity"; J. Bacteriol.; 185:4693-8.

Loiselle et al. (2003) "The Use of Cellulase in Inhibiting Biofilm Formation From Organisms Commonly Found on Medical Implants"; Biofouling; 19:77-85.

Roberfroid (2007) "Prebiotics: The Concept Revisited"; J. Nutr.; 137(3 Suppl 2):830S-7S.

Nivens et al. (2001) "Role of Alginate and Its O Acetylation in Formation of *Pseudomonas aeruginosa* Microcolonies and Biofilms"; J. Bacteriol.; 183:1047-57.

Wozniak et al. (2003) "Alginate is Not a Significant Component of TEH Extracellular Polysaccharide Matrix of PA14 and PAO1 *Pseudomonas aeruginosa* Biofilms"; Proc. Natl. Acad. Sci. USA; 100:7907-12.

Coticchia et al. (2006) "Presence and Density of Helicobacter Pylori Biofilms in Human Gastric Mucosa in Patients With Peptic Ulcer Disease"; J. Gastrointest. Surg.; 10:883-9.

Rouquette et al. (1996) "The Pathogenesis of Infection by Listeria Monocytogenes"; Microbiologia; 12:245-58.

Joshua et al. (2006) "Biofilm Formation in Campylobacter Jejuni"; Microbiology; 152(PT 2):387-96.

Lee et al. (2007) "Phenotypic and Functional Characterization of Bacillus anthracis Biofilms"; Microbiology; 153(PT 6):1693-701.

Tan et al. (2004) "A Movable Surface: Formation of *Yersinia* SP. Biofilms on Motile Caenorhabditis Elegans"; J. Bacteriol.; 186:5087-92.

Styer et al. (2005) "*Yersinia* Pestis Kills Caenorhabditis Elegans by a Biofilm-Independent Process That Involves Novel Virulence Factors"; EMBO Reports; 10:992-7.

Ledeboer et al. (May 2005) "Exopolysaccharide Sugars Contribute to Biofilm Formation by *Salmonella enterica* Serovar Typhimurium on HEP-2 Cells and Chicken Intestinal Epithelium"; J. Bacteriol.; 187(9):3214-3226.

Prouty et al. (2002) "Biofilm Formation and Interaction With the Surfaces of Gallstones by *Salmonella* SPP."; Infect. Immun.; 70:2640-9.

Knutton et al. (1984) "In Vitro Adhesion of Enterotoxigenic *Escherichia coli* to Human Intestinal Epithelial Cells From Mucosal Biopsies"; Infect. Immun.; 44:514-8.

* cited by examiner

METHODS OF COMPRISING SERRATIA PEPTIDASE FOR INHIBITION AND TREATMENT OF BIOFILMS RELATED TO CERTAIN CONDITIONS

PRIORITY CLAIM

The present application claims the benefit of U.S. Provisional Patent Application Ser. No. 61/263,776, filed Nov. 23, 2009, which application is incorporated herein by reference in its entirety.

BACKGROUND

A "biofilm" is a well known phenomenon and may be defined as a population of microbial cells growing on a surface and enclosed in a self-produced matrix of extracellular polymeric material, which mediates adhesion of the cells to each Other and to surfaces. Biofilms are not simply passive assemblages of cells that are stuck to surfaces, but are structurally and dynamically complex biological systems. As compared with cells that are planktonic in nature, bacteria growing in biofilms exhibit a different phenotype with respect to growth rate and gene transcription.

Unwanted biofilms have been responsible, for example, for the fouling of cooling-water towers, water pipelines, membrane units and food-processing plants. Biofilms are notoriously difficult to eradicate. Microbes in industrial biofilms are protected from antimicrobial chemicals, environmental bacteriophages, and phagocytic amoebae. (Donlan R M, Costerton J W. Biofilms: survival mechanisms of clinically relevant microorganisms. *Clin Microbiol Rev* 2002; 15167-293.)

In addition to their importance in industry, biofilms may be involved in a significant percentage of human microbial infections (Potera C. Forging a link between biofilms and disease. *Science* 1999; 283:1837-8). Parsek and Singh proposed four criteria for defining a biofilm etiology of an infection: the pathogenic bacteria are surface associated or adherent to a substratum; direct examination reveals bacteria in clusters, encased in a matrix of bacterial or host constituents; the infection is localized; and the infection is resistant to antibiotic therapy despite the antibiotic sensitivity of the constituent planktonic organisms (Parsek M R, Singh P K. Bacterial biofilms: an emerging link to disease pathogenesis. *Annu Rev Microbiol* 2003; 57:677-701.)

Biofilm infections can be involved in the etiology of dental caries, periodontal disease, cystic fibrosis (CF) airway infections, native valve endocarditis, chronic prostatitis, otitis media, and vaginal infections. Biofilm microorganisms are also involved in implant-related infections, in which adherent microbial populations form on the surfaces of catheters, prosthetic heart valves, joint replacements, and other devices (Donlan R M. Biofilms and device-associated infections. *Emerg Infect Dis* 2001; 7:277-81.)

The intestinal tract provides a reservoir for many antibiotic-resistant biofilm bacteria, including *Enterobacteriaceae* species, *Pseudomonas aeruginosa*, and *Acinetobacter* species (Donskey C J. The role of the intestinal tract as a reservoir and source for transmission of nosocomial pathogens. *Clin Infect Dis* 2004; 39:219-26.) The human opportunistic pathogen, *Pseudomonas aeruginosa*, is a major cause of infection-related mortality among the critically ill patients, and carries one of the highest case fatality rates of all gram-negative infections. Although the lungs have been traditionally considered to be a major site of *P. aeruginosa* infection among critically ill patients, a significant number of these infections arise as a result of direct contamination of the airways by the gastrointestinal flora or by hematogenous dissemination from the intestines to the lung parenchyma. Effective methods for the inhibition, reduction and/or treatment of *P. aeruginosa* would have a significant impact for this condition.

With respect to biofilms in the gut, it is now known that bacteria can exist for example as biofilms on the intestinal epithelium, within the mucus layer covering it, and on food particles in the lumen. (MacFarlane S, MacFarlane G T. Composition and metabolic activities of bacterial biofilms colonizing food residues in the gastrointestinal tract. *Appl Environ Microbiol* 2006; 72:6204-11; Probert H M, Gibson G R. Bacterial biofilms in the human gastrointestinal tract. *Curr Issues Intest Microbiol* 2002; 3:23-7.) Gastrointestinal biofilm-associated bacteria include *Bacteroides* ssp., *Clostridium* ssp., *Fusobacterium* ssp., *Klebsiella* ssp., *Spirochaetes* ssp., *Pseudomonas aeriginosa*, *Escherichia coli*, *Helicobacter pylori*, *Bifidobacterium* ssp., and gram-positive cocci.

Thus, there has gone unmet a need for improved methods, compositions, etc., related to reduction of biofilms within the ear, vagina, joints, bones, gut, surgical sites and other locations in mammals. The present methods, etc., provide one or more of these and/or other advantages.

SUMMARY

The present compositions, medicaments, therapeutics, systems, methods, etc., are directed to the reduction or inhibition of harmful biofilm(s) in animals, for example biofilms occurring in conjunction with certain diseases or conditions including bacterial vaginosis, bacterial vaginitis or fungal vaginitis (i.e., inflammations of the vagina due to bacteria or fungi); osteomyelitis; otitis media; chronic sinusitis; chronic prostatitis, native valve endocarditis; biofilm on a mucosal surface; and, biofilm infections of medical implants and medical devices. The compositions include physiologically acceptable anti-biofilm compositions comprising at least *Serratia* peptidase in a therapeutic amount. In some embodiments, the compositions further comprise therapeutic amounts of one or more of bromelain, papain, and a fibrinolytic enzyme. The fibrinolytic enzyme can be, for example, nattokinase, lumbrokinase or *Fusarium* protease. *Fusarium* protease is a fibrinolytic enzyme that has been reported to be more potent than nattokinase in its fibrinolytic activity.

The compositions are administered to the patient for a time sufficient to cause significant biofilm reduction on the target site, such as a mucosal surface, in the mammal. The compositions are administered, for example, as nutraceutical, therapeutic, or pharmaceutical compositions, and are typically suitable for oral ingestion by or topical application to mammals such as humans. The current discussion also includes methods of making and using or administering such compositions.

In another aspect, the present physiologically acceptable anti-biofilm compositions, methods, etc., are also directed to the use of digestive enzymes for the inhibition and reduction of pathogenic biofilm in the gastrointestinal tract of humans.

For example, the physiologically acceptable anti-biofilm compositions, methods, etc., can be directed to the use of cellulases, hemicellulases, lysozyme, pectinases, amylases, DNase I, $\beta$-1,6-N-acetylglucosaminidase, and other hydrolases that are capable of digesting the exopolysaccharide, exoprotein, and nucleotide matrix of biofilms.

The present physiologically acceptable anti-biofilm compositions, methods, etc., are also directed to oral physiologically acceptable anti-biofilm compositions for the inhibition and treatment of pathogenic gastrointestinal biofilms in humans.

In certain embodiments, the present physiologically acceptable anti-biofilm compositions, methods, etc., are directed to agents that are foodborne, waterborne or are nosocomial. Some embodiments are further directed to biofilm infections that are antibiotic-resistant and/or recurrent. The physiologically acceptable anti-biofilm compositions, etc., may be used in conjunction with antibiotics or antimicrobials. In addition these physiologically acceptable anti-biofilm compositions may be used in patients whose biofilm infections have failed to respond to antibiotics or antimicrobials.

The present physiologically acceptable anti-biofilm compositions, methods, etc., are also directed to the inhibition and treatment of biofilm infections caused by bioterrorist agents.

Thus, in one aspect, the present compositions, methods, etc., are directed to a physiologically acceptable anti-biofilm composition suitable for administration to a mammal, the composition comprising at least one pharmaceutically acceptable carrier and *Serratia* peptidase in amounts capable of significant biofilm degradation in the mammal upon administration to the mammal.

In some embodiments, the present compositions, methods, etc., further comprise one or more of bromelain, papain and a fibrinolytic enzyme. The fibrinolytic enzyme can comprise at least one of nattokinase or lumbrokinase, and the composition can be configured for oral administration such that the composition can capable of gastrointestinal absorption while retaining the anti-biofilm activity after passing through the stomach. The composition can also be administered via any other suitable route, such as topically, and other indirect or direct routes, such as buccal/sublingual, rectal, oral, nasal, vaginal, pulmonary, intraperitoneal, subcutaneous, intranasal, or intravenous.

The compositions, methods, etc., further can comprise at least one chelating agent capable of chelating at least one of calcium or iron configured for administration in an amount capable of significant biofilm degradation in the mammal. The chelating agent can be at least one of lactoferrin or a lactoferrin peptide capable of chelation.

The compositions, methods, etc., further can comprise at least one of an anti-biofilm acid-stable cellulase or an anti-biofilm anti-polymeric β-,6-N-acetyl-D-glucosamine (poly-β-,6-GlcNAc) agent, or at least one of an acid-stable hemicellulase/pectinase complex, β-gluconase, acid protease, or alkaline protease. The composition further can comprise at least one acid-stable agent selected from the following: a disaccharidase; amylase; α-amylase; β-amylase; glucoamylase; endoglucanase; xylanase; lipase; lysozyme; an enzyme with dipeptidyl peptidase IV (DPP-IV) activity; chitosanase; ficin; kiwi protease; any plant-derived protease or proteinase, or phytase. The composition further can comprise at least one acid-stable enzyme configured for administration in an amount capable of significant biofilm degradation in the mammal, the at least one enzyme selected from the following: 1,2-1,3-α-D-mannan mannohydrolase, 1,3-β-D-xylanxylanohydrolase, 1,3-β-D-glucan glucanohydrolase, 1,3(1,3;1,4)-α-D-glucan 3-glucanohydrolase, 1,3(1,3;1,4)-β-D-glucan 3(4)-glucanohydrolase, 1,3-1,4-α-D-glucan 4-glucanohydrolase, 1,4-α-D-glucan glucanohydrolase, 1,4-α-D-glucan glucohydrolase, 1,4-(1,3:1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5-α-L-arabinanohydrolase, 1,4-α-D-glucan maltohydrolase, 1,6-α-D-glucan 6-glucanohydrolase, 2,6-β-fructan fructanohydrolase, α-dextrin 6-glucanohydrolase, α-D-galactoside galactohydrolase, α-D-glucoside glucohydrolase, α-D-mannoside mannohydrolase, acylneuraminyl hydrolase, Aerobacter-capsular-polysaccharide galactohydrolase, β-D-fructofuranoside fructohydrolase, β-D-fucoside fucohydrolase, α-D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6-α-D-glucanohydrolase, glycoprotein-phosphatidylinositol phosphatidohydrolase, hyaluronate 4-glycanohydrolase, hyaluronoglucuronidase, pectin pectylhydrolase, peptidoglycan N-acetylmuramoylhydrolase, phosphatidylcholine 2-acylhydrolase, phosphatidylcholine 1-acylhydrolase, poly(1,4-α-D-galacturonide), poly(1,4-(N-acetyl-β-D-glucosaminide))-glycanohydrolase, proteases, sucrose α-glucosidase, triacylglycerol acylhydrolase, triacylglycerol protein-acylhydrolase.

The compositions, methods, etc., also can comprise a green tea extract, an acid-stable subtilisin or an acid-stable DNAse I, a chelating agent selected from the group comprising ethylenediamine-N,N,N',N'-tetraacetic acid (EDTA); the disodium, trisodium, tetrasodium, dipotassium, tripotassium, dilithium and diammonium salts of EDTA; the barium, calcium, cobalt, copper, dysprosium, europium, iron, indium, lanthanum, magnesium, manganese, nickel, samarium, strontium, and zinc chelates of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid)hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylene diamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11]pentatriacontane hexahydrobromide; triethylenetetraminie-N,N,N',N'',N''',N'''-hexaacetic acid; deferoxamine; deferiprone; and deferasirox.

The compositions, methods, etc., further can comprise, or exclude, an antibiotic, and can comprise quercetin, seaprose or *Fusarium* protease.

Another aspect herein is directed to methods of inhibiting a biofilm infection in a mammal comprising: identifying the presence of the biofilm infection, administering to the mammal a therapeutically effective amount of a composition comprising at least one pharmaceutically acceptable carrier and *Serratia* peptidase, bromelain, papain and a fibrinolytic enzyme in amounts capable of significant biofilm degradation in the mammal, in an amount and for a time sufficient to cause significant biofilm degradation within the mammal.

The methods further can comprise identifying the presence of the biofilm infection in the gastrointestinal system of the mammal, and orally administering to the mammal the therapeutically effective amount of the composition in an amount and for a time sufficient to cause significant biofilm degradation within the gut of the mammal.

The methods further can comprise identifying the presence of the biofilm infection at a surface of a body part of the mammal other than the gastrointestinal system, and topically administering to the surface of the body part the therapeutically effective amount of the composition in an amount and for a time sufficient to cause significant biofilm degradation at the surface of the body part. The surface can be for example exposed skin or an internal surface of the mammal. As with certain other methods and compositions herein, the methods can also comprise other routes and/or targets of administration.

The methods further can comprise administering at least one of lactoferrin and a chelating agent; at least one of an anti-biofilm acid-stable cellulase or an anti-biofilm antipolymeric β-1,6-N-acetyl-D-glucosamine (poly-β-1,6-GlcNAc) agent; or, at least one of an acid-stable hemicellulase/pectinase complex, β-gluconase, acid protease, or alkaline protease in an amount and for a time sufficient to cause significant biofilm degradation within of the mammal.

The methods further can comprise administering at least one an acid-stable agent, for example selected from the following: a disaccharidase; amylase; α-amylase; β-amylase; glucoamylase; endoglucanase; xylanase; lipase; lysozyme; an enzyme with dipeptidyl peptidase IV (DPP-IV) activity; chitosanase; ficin; kiwi protease; any plant-derived protease or proteinase, or phytase. The methods also can comprise administering at least one an acid-stable selected from the following: 1,2-1,3-α-D-mannan mannohydrolase, 1,3-β-D-xylanxylanohydrolase, 1,3-β-D-glucan glucanohydrolase, 1,3(1,3;1,4)-α-D-glucan 3-glucanohydrolase, 1,3(1,3;1,4)-β-D-glucan 3(4)-glucanohydrolase, 1,3-1,4-α-D-glucan 4-glucanohydrolase, 1,4-α-D-glucan glucanehydrolase, 1,4-α-D-glucan glucohydrolase, 1,4-(1,3: 1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5-α-L-arabinanohydrolase, 1,4-α-D-glucan maltohydrolase, 1,6-α-D-glucan 6-glucanohydrolase, 2,6-β-fructan fructanohydrolase, α-dextrin 6-glucanohydrolase, α-D-galactoside galactohydrolase, α-D-glucoside glucohydrolase, α-D-mannoside mannohydrolase, acylneuraminyl hydrolase, Aerobacter-capsular-polysaccharide galactohydrolase, β-D-fructofuranoside fructohydrolase, β-D-fucoside fucohydrolase, α-D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6-α-D-glucanohydrolase, glycoprotein-phosphatidylinositol phosphatidohydrolase, hyaluronate 4-glycanohydrolase, hyaluronoglucuronidase, pectin pectylhydrolase, peptidoglycan N-acetylmuramoylhydrolase, phosphatidylcholine 2-acylhydrolase, phosphatidylcholine 1-acylhydrolase, poly (1,4-α-D-galacturonide), poly(1,4-(N-acetyl-β-D-glucosaminide))-glycanohydrolase, proteases, sucrose α-glucosidase, triacylglycerol acylhydrolase, triacylglycerol protein-acylhydrolase.

The methods further can comprise administering at least one of an acid-stable subtilisin and an acid-stable DNAse I in an amount and for a time sufficient to cause significant biofilm degradation within of the mammal. The methods can also comprise: identifying the presence of at least one of *Clostridium* ssp, *Klebsiella* ssp, *Pseudomonas* ssp, *Bacteroides* ssp, *Enterococcus* ssp, *Campylobacter* ssp, *Bacillus* ssp, *Yersinia* ssp, *Brucella* ssp, *Salmonella* ssp, *Shigella* ssp, *Fusobacterium* ssp, *Spirochaetes* ssp, *Entamoeba* ssp, *Candida* ssp, *Escherichia coli*, *Vibrio cholerae*, *Staphylococcus* ssp, *Streptococcus* ssp, *Hemophilus* ssp, *Aspergillus* ssp and *Gardnerella* ssp in the mammal, and, administering to the mammal a therapeutically effective amount of the anti-biofilm *Serratia* peptidase agent for a time sufficient to treat the identified microorganism.

The methods can comprise administering, or not administering, an antibiotic in conjunction with the *Serratia* peptidase, and other possible elements of the composition as discussed herein. The methods further can also comprise administering one or more of an quercetin, seaprose or *Fusarium* protease in an amount and for a time sufficient to cause significant biofilm degradation within of the mammal.

In a further aspect, the methods comprise inhibiting at least one of bacterial vaginosis, bacterial vaginitis or fungal vaginitis in a mammal, the methods comprising: identifying the presence of the at least one of bacterial vaginosis, bacterial vaginitis or fungal vaginitis, administering to the mammal a therapeutically effective amount of a composition comprising at least one pharmaceutically acceptable carrier and *Serratia* peptidase, in an amount capable of significant reduction of the bacterial vaginosis, bacterial vaginitis or fungal vaginitis in the mammal, in an amount and for a time sufficient to cause significant bacterial vaginosis, bacterial vaginitis or fungal vaginitis reduction within the mammal. In another aspect, the methods comprise inhibiting otitis media in a mammal, the methods comprising: identifying the presence of the otitis media, administering to the mammal a therapeutically effective amount of a composition comprising at least one pharmaceutically acceptable carrier and *Serratia* peptidase, in an amount capable of significant reduction of the otitis media in the mammal, in an amount and for a time sufficient to cause significant otitis media reduction within the mammal. In yet another aspect, the methods comprise inhibiting osteomyelitis in a mammal, the methods comprising: identifying the presence of the osteomyelitis, administering to the mammal a therapeutically effective amount of a composition comprising at least one pharmaceutically acceptable carrier and *Serratia* peptidase, in an amount capable of significant osteomyelitis reduction in the mammal, in an amount and for a time sufficient to cause significant osteomyelitis reduction within the mammal. And, in a further aspect, the methods comprise inhibiting a biofilm on a mucosal surface in a mammal, the method comprising: identifying the presence of the biofilm on a mucosal surface, administering to the mammal a therapeutically effective amount of a composition comprising at least one pharmaceutically acceptable carrier and *Serratia* peptidase, in an amount capable of significant biofilm reduction on the mucosal surface in the mammal, in an amount and for a time sufficient to cause significant biofilm reduction on the mucosal surface within the mammal. Such methods can further comprise one or more of the other features discussed herein.

These and other aspects, features, and embodiments are set forth within this application, including the following Detailed Description. Unless expressly stated otherwise, all embodiments, aspects, features, etc., can be mixed and matched, combined, and permuted in any desired manner.

DETAILED DESCRIPTION

Biofilms in mammals have been implicated in a variety of possible diseases, either as causing such diseases or making them worse. The present compositions, systems, methods, etc., are directed to the reduction of biofilm(s) in certain sites and/or associated with certain diseases or disorders in animals, including bacterial vaginosis, bacterial vaginitis or fungal vaginitis; osteomyelitis; otitis media; chronic sinusitis; biofilm on a mucosal surface; and, biofilm infections of medical implants and medical devices. The methods include inhibiting, treating, or reducing biofilms in such locations.

Exemplary Enzymes That Treat, Inhibit, Etc., Biofilms

Enzymes that disrupt the biofilm matrices of these organisms within the gastrointestinal tract or other target area are the subject of the methods, etc., herein.

Serratia Peptidase

Serratia peptidase, also known as serrapeptase, is a known enzyme that is an extracellular metalloprotease produced by Serratia sp. E15. Serratia peptidase is known to be absorbed in the GI tract. Serratia peptidase can be enterically coated for example as tablets, and formulations including monovalent alginate. Tablets of Serratia peptidase (5 mg/tablet) are marketed as Danzen or Dasen™ (Takeda Chemical Industries, Ltd.), Aniflazym® (Takeda Pharma GmbH) and Serodase (Hayat Pharmaceutical Industries, Ltd.) Serratia peptidase may have been sold for use as an anti-inflammatory, analgesic and mucolytic.

Bromelain & Papain

Bromelain and papain are known enzymes and are known to be active within the gastrointestinal tract. Oral bromelain may have been reported to inhibit enterotoxigenic E. Coli attachment to the small intestine in piglets, possibly by modifying receptor attachment sites. Bromelain is absorbed through the intestine and it has anti-edema, anti-inflammatory and anti-coagulation effects. Oral bromelain has been reported to attenuate inflammation in a murine model of asthma and to inhibit lung metastases.

Phlogenzym® (Mucos Pharma GmbH & Co.) includes bromelain (90 mg), trypsin (48 mg) and the antioxidant flavonoid, rutin (100 mg) and has been reported to reduce inflammation and experimental allergic encephalomyelitis. Wobenzym® N is reportedly a combination of bromelain, papain, trypsin, chymotrypsin, and rutin. Wobe-Mugos®, reportedly contains trypsin, chymotrypsin and papain, has been reported to be as effective as acyclovir in the treatment of herpes zoster.

Lactoferrin

Lactoferrin is also known as lactotransferrin. It is a naturally-occurring molecule, and is an extracellular iron-binding glycoprotein which can be found in mucosal secretions, including those found in the respiratory tract, gastrointestinal tract, and urogenital tract. It is also released by neutrophils at sites of infection. During infection, the binding of iron by lactoferrin is proposed to reduce the amount of free extracellular iron. This process, known as the hypoferremia of infection, is thought to further limit the free iron available to invading microorganisms. Lactoferrin can be absorbed through the intestines. Enteric-formulated lactoferrin is more efficiently absorbed from the intestine than is non-enteric-formulated lactoferrin.

To applicant's knowledge, lactoferrin has not been combined with Serratia peptidase, bromelain or papain.

Otitis Media

Otitis media has been described as an inflammation of the middle ear that is common in children.

Vaginosis

Bacterial vaginosis (BV) is a common lower genital tract syndrome affecting women of reproductive age. BV is associated with adverse outcomes among nonpregnant and pregnant women. BV has been found to be associated with preterm labor, preterm delivery, low birth weight, postcesarean endometritis, and postabortion pelvic inflammatory disease. BV occurs when there are changes of the normal flora of the vagina, causing an increased prevalence of Gardnerella vaginalis, Mycoplasma hominis, and anaerobic organisms and a decreased prevalence of the normally predominant Lactobacillus species. Previous studies have shown that the alteration of the normal flora may increase the risk of acquiring BV, HIV type 1, or other sexually transmitted diseases.

To applicant's knowledge, treatments recommended by the Centers for Disease Control (CDC) for BV include metronidazole or clindamycin administered orally or intravaginally. Metronidazole is a nitroimidazole with activity against anaerobic organisms, while clindamycin, a macrolide, has a broad spectrum of activity against a variety of microbes including aerobic and anaerobic organisms. The CDC recommends oral metronidazole for 7 days or vaginal metronidazole gel for 5 days, as they are equally effective. Metronidazole offers average cure rates of 80% to 90%. Also, metronidazole is thought to be most effective for treating infection that has spread into the upper reproductive tract. The CDC also recommends clindamycin cream 2% for 7 days, while noting that it might not be as effective as metronidazole.

Despite treatment with either metronidazole or clindamycin, similar percentages of women (approximately 10 to 15%) fail therapy after 1 month. The proportion of women who relapse also increases over time. The recurrence rate of BV is approximately 30% at 3 months and approximately 50 to 80% at 1 year following therapy with either drug. Clindamycin's relapse rate is higher: 4 weeks after clindamycin treatment, 56% of women have recurring bacterial vaginosis. Current therapy for managing recurrent BV is repeated treatment with antibiotics. An obvious problem and important health issue associated with repeated exposure to the same antibiotic is resistance of those microbes targeted by the drug, which can result in an alteration of flora and possible persistence of BV-associated pathogens.

Recent studies have shown an emergence of clindamycin-resistant genital organisms among clinically relevant bacteria, including group B streptococci. Resistance of BV to oral metronidazole has been postulated to result from the adherent G. vaginalis biofilm that persists after standard therapy. In vitro models for G. vaginalis biofilm have been developed.

Orthopedic Implants and Medical Devices

Implant-related infections are difficult to treat with antimicrobial agents alone. Several groups have reported on the properties of implant-associated biofilms and on the need for ancillary or adjunct therapies.

The compositions and methods herein may not only treat but may inhibit or prevent implant-related infections via chronic administration of safe and effective oral compositions without antibiotics.

Other Enzymes and Molecules

In one aspect the suitable, physiologically acceptable anti-biofilm compositions, etc., herein further comprise an amount of quercetin, seaprose (also known as seaprose-S) and/or Fusarium protease in conjunction with the Serratia peptidase, bromelain, papain and a fibrinolytic enzyme, in an amount and for a time sufficient to cause significant biofilm degradation within of the mammal.

Quercetin is an anti-inflammatory bioflavonoid. The composition is claimed for the treatment of non-bacterial cystitis. It has been reported that quercetin alone does not have a high bioavailability due to the fact that transmural intestinal absorption is relatively low.

Seaprose, also known as Protease S or Seaprose S, is a semi-alkaline serine-proteinase produced by the fungus *Aspergillus melleus*. Seaprose-S reportedly demonstrates an ability to reduce painful inflammation and break up mucus.

In one aspect the suitable, physiologically acceptable anti-biofilm compositions, etc., herein further comprise an amount of anti-polymeric β-1,6-N-acetyl-D-glucosamine (poly-β-1,6-GlcNAc) agents to substantially disperse poly-β-1,6-GlcNAc and thus capable of significant biofilm degradation. E.g., see Itoh Y, Wang X, Hinnebusch B J, Preston J F, Romeo T. Depolymerization of β-1,6-N-acetyl-D-glucosamine disrupts the integrity of diverse bacterial biofilms. *J Bacteriol* 2005;187;382-7) In some embodiments, for this and other agents, either alone or in combination, such significant reduction means, if measured in vitro, a log reduction of 1, typically 1.5, or 3.0-3.8 or better. In vivo, such significant reduction can be substantial reduction of one or more symptoms associated with a biofilm infection, or even substantial elimination of one or more symptoms associated with a biofilm infection. Exemplary anti-GlcNAc-agents include a previously identified β-hexosaminidase and biofilm-dispersing enzyme of *A. actinomycetemcomitans*, DspB or dispersin B, which specifically hydrolyzes the glycosidic linkages of poly-β-1,6-GlcNAc and disrupts bacterial biofilm (Kaplan J B, Ragunath C, Ramasubbu N, Fine D H. 2003. Detachment of *Actinobacillus actinomycetemcomitans* biofilm cells by an endogenous β-hexosaminidase activity. *J Bacteriol* 2003;185: 4693-8). Dispersin B cleaves β(1,6)-linked N-acetylglucosamine polymer using a catalytic machinery similar to other family 20 hexosaminidases which cleave β(1,4)-linked N-acetylglucosamine residues. Dispersin B and similar hexosaminidases with activity in biofilms are suitable for use in the methods, physiologically acceptable anti-biofilm compositions, etc., discussed herein. The anti-poly-β-1,6-GlcNAc agents can be used with, or instead of, cellulase, discussed further below, although typically they are used together.

In one aspect the suitable, physiologically acceptable anti-biofilm compositions comprise a cellulase in an amount capable of significant biofilm degradation. Such cellulases can have activity, against, for example, cellulose in a *Salmonella* biofilm or others. Cellulase refers to a class of enzymes produced chiefly by fungi, bacteria, and protozoans that catalyze the hydrolysis of cellulose. However, there are also cellulases produced by other types of organisms such as plants and animals. Cellulases that have been used as digestive enzymes are known to be acid-stable. These include but are not limited to cellulases from *Aspergillus* species. Several different kinds of cellulases are known, which differ structurally and mechanistically. The EC number for this group of enzymes is EC 3.2.1.4. The reaction catalyzed is the endohydrolysis of 1,4-β-D-glycosidic linkages in cellulose. Other names for cellulase are: Endoglucanase, endo-1,4-β-glucanase, carboxymethyl cellulose, endo-1,4-β-D-glucanase, β-1,4-glucanase, β-1,4-endoglucan hydrolase, celludextrinase, avicelase. Cellulases have been used in vitro in the disruption of biofilms on medical implants under acidic pH conditions (Loiselle M, Anderson K W, The use of cellulase in inhibiting biofilm formation from organisms commonly found on medical implants. *Biofouling* 2003;19:77-85.) In typical embodiments, the cellulase(s) herein are resistant to denaturation/inactivation at a pH range of 1.0 to 5.0 and 10 to 14, possesses hydrolytic activity across a pH span of 1 to 14, has effective hydrolytic activity within the gastric environment at a fasting pH of 1.0 to 3.0 and in the presence of food and other ingested material, and/or possesses effective hydrolytic activity at a pH of 4.5 to 7.5 encompassing physiologic pH in the small intestines and colon.

Commercial sources of cellulases, hemicellulases and other enzymes that may be used include the following: Deerland Enzymes, Kennesaw, Ga.; National Enzyme Company, Specialty Enzymes; and others. The enzymes may be derived from any suitable source such as plant, bacterial, fungal or animal sources.

In one embodiment, the anti-biofilm compositions herein further comprise physiologically acceptable cellulase, hemicellulase/pectinase complex, β-gluconase, acid protease, and alkaline protease, with at least one pharmaceutically acceptable carrier, diluents, excipients, buffers, or adjuvants. Pharmaceutically acceptable carriers or diluents, excipients, buffers, adjuvants, and the like are nontoxic to recipients at the dosages and concentrations employed.

In one embodiment, the amount of cellulase per oral dose is about 100-300 CU, and typically about 200 CU; the amount of hemicellulase/pectinase complex is about 60-100 HSU, and typically about 80 HSU; the amount of βgluconase is about 6-10 BGU, and typically about 8 BGU; the amount of acid protease is about 15-25 SAP, and typically about 20 SAP; and, the amount of alkaline protease is about 15-25 HUT, and typically about 20 HUT.

In still further embodiments, the amount of cellulase per oral dose ranges from 1 to 10,000 CU, the amount of hemicellulase/pectinase complex ranges from 1 to 8,000 HSU, the amount of β-gluconase ranges from 1 to 1000 BGU, the amount of acid protease ranges from 1 to 10,000 SAP, and the amount of alkaline protease ranges from 1 to 40,000 HUT.

In a further embodiment, the physiologically acceptable anti-biofilm composition comprises cellulase, hemicellulase/pectinase complex, β-gluconase, acid protease, alkaline protease, and any one or more of the following in an amount capable an amount capable of significant biofilm degradation: disaccharides, amylase, -amylase, β-amylase, glucoamylase, endoglucanase, xylanase, lipase, lysozyme, any enzyme such as a protease, peptidase or protease/peptidase complex with dipeptidyl peptidase IV (DPP-IV) activity, chitosanase, bromelain, papain, ficin, kiwi protease, any plant-derived protease or proteinase, or phytase.

In a further embodiment, the physiologically acceptable anti-biofilm composition is composed of cellulase, hemicellulase/pectinase complex, β-gluconase, acid protease, alkaline protease, and any one or more of the following specific enzymes in an amount capable of biofilm degradation: 1,2-1,3- -D-mannan mannohydrolase, 1,3-β-D-xylanxylanohydrolase, 1,3-β-D-glucan glucanohydrolase, 1,3(1,3;1,4)--D-glucan 3-glucanohydrolase, 1,3(1,3;1,4)-β-D-glucan 3(4)-glucanohydrolase, 1,3-1,4- -D-glucan 4-glucanohydrolase, 1,4- -D-glucan glucanehydrolase, 1,4- -D-glucan glucohydrolase, 1,4-(1,3:1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5- -L-arabinanohydrolase, 1,4- -D-glucan maltohydrolase, 1,6- -D-glucan 6-glucanohydrolase, 2,6-β-fructan fructanohydrolase, -dextrin 6-glucanohydrolase, -D-galactoside galactohydrolase, -D-glucoside glucohydrolase, -D-mannoside mannohydrolase, acylneuraminyl hydrolase, Aerobacter-capsular-polysaccharide galactohydrolase, β-D-fructofuranoside fructohydrolase, β-D-fucoside fucohydrolase, -D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6- -D-glucanohydrolase, glycoprotein-phosphatidylinositol phosphatidohydrolase, hyaluronate 4-glycanohydrolase, hyaluronoglucuronidase, pectin pectyl-hydrolase, peptidoglycan N-acetylmuramoylhydrolase, phosphatidylcholine 2-acylhydrolase, phosphatidylcholine 1-acylhydrolase, poly(1,4- -D-galacturonide), poly(1,4-(N-acetyl-β-D-glucosaminide))-glycanohydrolase, proteases, sucrose -glucosidase, triacylglycerol acylhydrolase, triacyl-glycerol protein-acylhydrolase.

Another group of enzymes that may be employed in the methods, etc. herein is a sub-group of serine proteases commonly designated as subtilisins. A subtilisin is a serine protease produced by Gram-positive bacteria or fungi. The amino acid sequences of a number of subtilisins have been determined, including at least six subtilisins from *Bacillus* strains, namely, subtilisin 168, subtilisin BPN, subtilisin Carlsberg, subtilisin DY, subtilisin amylosacchariticus, and mesentericopeptidase, one subtilisin from an actinomyc-etales, thermitase from *Thermoactinomyces vulgaris*, and one fungal subtilisin, proteinase K from *Tritirachium album*.

An exemplary lipase as discussed above can be a microbial lipase. As such, the lipase may be selected from yeast lipases, e.g., *Candida*, and bacterial lipases, e.g., *Pseudomonas* or *Bacillus*, lipases; or fungal, e.g., *Humicola* or *Rhizomucor*.

Examples of amylases useful in the methods, etc., herein include *Bacillus* amylases, e.g., *Bacillus stearothermophilus* amylase, *Bacillus amyloliquefaciens* amylase, *Bacillus subtilis* amylase or *Bacillus licheniformis* amylase or *Aspergillus* amylases, e.g., *Aspergillus niger* or *Aspergillus oryzae* amylase.

Another group of enzymes useful in the methods, etc., herein include pectinases belonging to the enzyme classes polygalacturonases (EC3.2.1.15), pectinesterases (EC3.2.1.11), pectin lyases (EC4.2.2.10) and hemicellulases such as endo-1,3-β-xylosidase (EC 3.2.1.32), xylan 1,4-β-xylosidase (EC 3.2.1.37) and -L-arabinofuranosidase (EC 3.2.1.55). A suitable source organism for pectinases may be *Aspergillus niger* or *Aspergillus aculeatus*.

Lysozyme, also known as muramidase or N-acetylmuramide glycanhydrolase, is a 14.4 kilodalton enzyme (EC 3.2.1.17) that damages bacterial cell walls by catalyzing hydrolysis of 1,4-β-linkages between N-acetylmuramic acid and N-acetyl-D-glucosamine residues in a peptidoglycan and between N-acetyl-D-glucosamine residues in chitodextrins. Lysozyme is found in saliva, tears, and polymorphonucleocytes and has known antibacterial activity. The enzyme functions by attacking peptidoglycans (found in the cells walls of bacteria, especially Gram-positive bacteria) and hydrolyzing the glycosidic bond that connects N-acetyl-muramic acid with the fourth carbon atom of N-acetylglucosamine. Lysozyme has been used in the treatment of otitis media and sinusitis (U.S. Pat. No. 7,060,674). Oral lysozyme compositions have been used in the treatment of various conditions in humans, including arthritis (U.S. Pat. No. 7,229,809).

Another enzyme that may be employed in the methods, etc. herein is deoxyribonuclease I (DNase I), a phosphodi-esterase capable of hydrolyzing polydeoxyribonucleic acid. DNase I has been purified from various species to various degrees. DNase I, when inhaled, affects the capability of *P. aeruginosa* to form biofilms in the lungs in the initial development stages. DNase I hydrolyzes the DNA present in sputum/mucus of cystic fibrosis patients and reduces viscosity in the lungs, promoting improved clearance of secretions. Enzymes that are acid-stable are candidates for use in conjunction with the methods, physiologically acceptable anti-biofilm compositions, etc., discussed herein. DNase I activities are classifiable into three groups on the basis of their different tissue distributions of DNase I. DNase I of parotid type is secreted from the parotid gland and must pass through the very acidic conditions in the stomach.

The physiologically acceptable anti-biofilm compositions, methods, etc., herein are to be taken by mouth, typically at least 1 hour before or +2-hours after a meal or consumption of food. The physiologically acceptable anti-biofilm compositions, methods, etc., herein are typically to be taken 2 to 4 times per day (other intervals may be appropriate in certain circumstances) and the regimen is typically to be followed for an extended period, for example at least about 1 or 2 months.

The enzyme preparations may be combined with a natural antimicrobial such as oil of oregano, berberine, or undecylenic acid or with a prescription antibiotic or antimicrobial.

The enzyme preparations may be combined with the oral intake of one or more probiotic microorganisms or prebiotic compositions. For example, such preparations can be consumed in the same composition as a probiotic microorganisms or prebiotic composition, simultaneously with such probiotic microorganisms or prebiotic compositions, or separately but in conjunction with such probiotic microorganisms or prebiotic compositions. The World Health Organization defines probiotic organisms as live microorganisms that when administered in adequate amounts confer a health benefit on the host. The enzyme preparation may be combined with one or more prebiotics. A prebiotic is defined as "selectively fermented ingredients that allow specific changes, both in the composition and/or activity in the gastrointestinal microflora that confer benefits upon host well-being and health." (Roberfroid M. Prebiotics: the concept revisited. *J Nutr* 2007;137(3 Suppl 2):830S-7S.)

Methods related to the compositions, etc., herein include methods of screening, making and using, including for the manufacture of medicaments.

In some aspects, the methods comprise inhibiting a biofilm infection in a mammal, for example gastrointestinal or at one of the other target sites discussed herein, the method comprising: identifying the presence of the biofilm infection, administering, orally or otherwise, to the mammal a therapeutically effective amount of at least one anti-biofilm agent comprising at least one pharmaceutically acceptable carrier and a therapeutic amount of *Serratia* peptidase, in amounts capable of significant biofilm degradation in the mammal upon administration to the mammal. In further embodiments the methods comprise administering one or more of bromelain, papain and a fibrinolytic enzyme with the *Serratia* peptidase, and one or more of the other aspects or elements of the compositions, etc., herein.

The compositions herein can be for use as an active therapeutic substance, for use in the manufacture of a medicament for inhibiting or treating a gastrointestinal biofilm in a mammal, or for manufacturing a medicament able to reduce symptoms associated with a gastrointestinal biofilm in a human patient, for example comprising combining a pharmaceutically effective amount of and a therapeutic amount of *Serratia* peptidase in an amount capable of significant biofilm degradation with at least one of a pharmaceutically acceptable carrier, adjuvant, excipient, buffer and diluent. In further embodiments the methods further comprise administering one or more of bromelain, papain and a fibrinolytic enzyme with the *Serratia* peptidase, Exemplary Biofilm Targets Exemplary target biofilm organisms, including both indigenous and biofilm infectious organisms are discussed below.

*Enterococci*

*Enterococci*, although part of the normal flora of the human gastrointestinal tract, have been recognized as an important cause of nosocomial infection for over two decades and are commonly implicated in urinary tract infections, bacteremia, intra-abdominal and surgical wound infections, catheter-related infections, and endocarditis.

*Staphylococcus*

Pathogenic staphylococci can form biofilms in which they show a higher resistance to antibiotics and the immune defense system than their planktonic counterparts. *Staphylococcus aureus* is a common pathogen associated with nosocomial infections. It can persist in clinical settings and gain increased resistance to antimicrobial agents through biofilm formation. *Staphylococcus aureus* is among the leading pathogens causing bloodstream infections able to form biofilms on host tissue and indwelling medical devices and to persist and cause disease. Infections caused by *S. aureus* are becoming more difficult to treat because of increasing resistance to antibiotics (e.g., vancomycin or methicillin-resistant *Staphylococcus aureus*). In a biofilm environment particularly, microbes exhibit enhanced resistance to antimicrobial agents.

*Pseudomonas*

The human opportunistic pathogen, *Pseudomonas aeruginosa*, is a major cause of infectious-related mortality among the critically ill patients, and carries one of the highest case fatality rates of all gram-negative infections. Although the lungs have been traditionally considered to be a major site of *P. aeruginosa* infection among critically ill patients, a significant number of these infections arise as a result of direct contamination of the airways by the gastrointestinal flora or by hematogenous dissemination from the intestine to the lung parenchyma. *Pseudomonas aeruginosa* causes severe infections in immunologically compromised patients and is a major pathogen in cystic fibrosis patients. An important virulence mechanism is the formation of a mucoid biofilm. Secreted alginate is a crucial constituent of the mucoid biofilm matrix. However, alginate-negative mutants of *P. aeruginosa* are also able to form nonmucoid biofilms, showing an architecture different from that of biofilms formed by alginate-overproducing mucoid *P. aeruginosa* (Nivens D E, Ohman D E, Williams J, Franklin M J. Role of alginate and its O acetylation in formation of *Pseudomonas aeruginosa* microcolonies and biofilms. *J Bacteriol* 2001; 183:1047-57; Wozniak D J, Wyckoff T J, Starkey M, Keyser R, Azadi P, O'Toole G A, Parsek M R. Alginate is not a significant component of the extracellular polysaccharide matrix of PA14 and PAO1 *Pseudomonas aeruginosa* biofilms. *Proc Natl Acad Sci USA* 2003;100:7907-12.)

*Helicobacter Pylori*

*H. pylori* is one of the more common human pathogens infecting 50% of the world's population. It is associated with duodenal ulcers, gastric ulcers, gastritis, and gastric carcinoma. Treatment of *H. pylori* is difficult involving multidrug regimens and lengthy treatment periods. There is a 10-20% relapse rate. Recent studies document the importance of biofilms in the pathogenesis of *H. pylori* disease. (Coticchia J M et al. Presence and density of *Helicobacter pylori* biofilms in human gastric mucosa in patients with peptic ulcer disease. J Gastrointest Surg. 2006;10:883-9) An oral multienzyme formulation holds great promise to facilitate the elimination of *H. pylori* biofilm and the eradication of *H. pylori* pathogens thereby reducing the risk of gastritis, peptic ulcer disease, and gastric cancer.

*Listeria*

The foodborne pathogen *Listeria* is the causative agent of listeriosis, a severe disease where the overt form has a severe mortality greater than 25%. *Listeria monocytogenes* can survive and grow over a wide range of environmental conditions such as refrigeration temperatures, low pH and high salt concentration. This allows the pathogen to overcome food preservation and safety barriers, and pose a potential risk to human health. *Listeria monocytogenes* may specifically be found in raw foods, such as unpasteurized fluid milk, raw vegetables, raw and cooked poultry. It has the ability to grow at low temperatures; thus, allowing it to grow in refrigerated foods. *Listeria monocytogenes* was thought to be exclusively associated as infections in animals, but recently, this pathogenic species has also been isolated, in its dormant form, in the intestinal tract of small percentage of the human population (Rouquette C, Berche P. The pathogenesis of infection by *Listeria monocytogenes*. *Microbiologia* 1996;12:245-58).

*Campylobacter*

*Campylobacter jejuni* is a species of curved, rod-shaped, Gram-negative microaerophilic, bacteria commonly found in animal feces. It is one of the most common causes of human gastroenteritis in the world. Food poisoning caused by *Campylobacter* species can be severely debilitating but is rarely life-threatening. It has been linked with subsequent development of Guillain-Barré syndrome (GBS), which usually develops two to three weeks after the initial illness. Contaminated food is a major source of isolated infections, with incorrectly prepared meat and poultry normally the source of the bacteria. Infection with *C. jejuni* usually results in enteritis, which is characterized by abdominal pain, diarrhea, fever, and malaise. The major gastrointestinal pathogen *Campylobacter jejuni* is shown to exist as three forms of monospecies biofilm in liquid culture. (Joshua G W, Guthrie-Irons C, Karlyshev A V, Wren B W. Biofilm formation in *Campylobacter jejuni*. *Microbiology* 2006; 152(Pt 2):387-96.)

*Bacillus Anthracis*

*Bacillus anthracis* is a Gram-positive, endospore-forming bacterium and is the aetiological agent of pulmonary, gastrointestinal and cutaneous anthrax. In endemic areas in which humans and livestock interact, chronic cases of cutaneous anthrax are commonly reported. Currently, there are few data known to the inventor that account for the importance of the biofilm mode of life in *B. anthracis*, yet biofilms have been characterized in other pathogenic and non-pathogenic *Bacillus* species, including *Bacillus cereus* and *Bacillus subtilis*, respectively. *B. anthracis* readily forms biofilms which are inherently resistant to commonly prescribed antibiotics. (Lee K, Costerton J W, Ravel J, Auerbach R K, Wagner D M, Keim P, Leid J G. Phenotypic and functional characterization of *Bacillus anthracis* biofilms. *Microbiology* 2007;153(Pt 6):1693-701.)

*Yersinia*

Yersiniosis is an infectious disease caused by a bacterium of the genus *Yersinia*. In the United States, most human illness is caused by one species, *Y. enterocolitica*. Infection with *Y. enterocolitica* occurs most often in young children. Common symptoms in children are fever, abdominal pain, and diarrhea. Gastrointestinal symptoms are common in both the acute and chronic states of yersiniosis. Infection is most often acquired by eating contaminated food, especially raw or undercooked pork products. Drinking contaminated unpasteurized milk or untreated water can also transmit the infection.

*Yersinia pestis*, the causative agent of bubonic plague, is transmitted to rodents and humans by the bites of fleas whose proventriculi are blocked by a dense mass of the biofilm bacteria. (Tan L, Darby C. A movable surface: formation of *Yersinia* sp. biofilms on motile *Caenorhabditis elegans*. J Bacteriol. 2004;186:5087-92.) The blockage starves the flea and stimulates it to bite repeatedly in search of blood meals, thus spreading the bacteria to new hosts. Biofilm models using *Caenorhabditis elegans* may be used to identify enzymes that kill *Yersinia* biofilms (Styer K L, Hopkins G W, Bartra S S, Plano G V, Frothingham R, Aballay A. *Yersinia pestis* kills *Caenorhabditis elegans* by a biofilm-independent process that involves novel virulence factors. *EMBO reports* 2005;10:992-7.)

*Brucella* Species

Humans are generally infected in one of three ways: eating or drinking something that is contaminated with *Brucella*, breathing in the organism (inhalation), or having the bacteria enter the body through skin wounds. The most common way to be infected is by eating or drinking contaminated milk products.

Salmonella

*Salmonella enterica*, a foodborne pathogen that causes salmonellosis, is caused by the ingestion of bacteria that invade the intestinal epithelium and multiply there. *Salmonella enterica* is known to form biofilms, and its attachment to, and growth on, eukaryotic cells is facilitated by exopolysaccharides (Ledeboer & Jones, 2005). Most persons infected with *Salmonella* develop diarrhea, fever, and abdominal cramps 12 to 72 hours after infection. The illness usually lasts 4 to 7 days, and most persons recover without treatment. However, in some persons the diarrhea may be so severe that the patient needs to be hospitalized. In these patients, the *Salmonella* infection may spread from the intestines to the blood stream, and then to other body sites and can cause death unless the person is treated promptly.

Shigella

There are several different kinds of *Shigella* bacteria: *Shigella sonnei*, also known as "Group D" *Shigella*, accounts for over two-thirds of the shigellosis in the United States. Shigellosis is an infectious disease caused by a group of bacteria called *Shigella*. Most who are infected with *Shigella* develop diarrhea, fever, and stomach cramps starting a day or two after they are exposed to the bacterium. Some *Shigella* bacteria have become resistant to antibiotics. A second type, *Shigella flexneri*, or "group B" *Shigella*, accounts for almost all of the rest. Other types of *Shigella* continue to be important causes of disease in the developing world. One type found in the developing world, *Shigella dysenteriae* type 1, causes deadly epidemics there.

*Typhi* (Typhoid Fever)

*Salmonella enterica* serovar *Typhi* causes typhoid fever, an enteric fever that is potentially fatal. Asymptomatic carriers may carry bacteria in the gallbladder. *Salmonella typhi* lives only in humans. Persons with typhoid fever carry the bacteria in their bloodstream and intestinal tract. In addition, a small number of persons, called carriers, recover from typhoid fever but continue to carry the bacteria. Both ill persons and carriers shed *S. typhi* in their feces (stool). *Salmonella typhi* is transmitted in contaminated food, water and beverages. A system was recently developed to analyze *salmonella* biofilm formation on glass coverslips (Prouty A M, Schwesinger W H, Gunn J S. Biofilm formation and interaction with the surfaces of gallstones by *Salmonella* spp. *Infect Immun* 2002;70:2640-9.)

*Escherichia Coli*

Enterotoxigenic *Escherichia coli* targets the small intestine where the barrier effect of the autochthonous microflora is low due to higher acidity and peristaltic movements in this region. This organism adheres to and colonizes the mucus in order to elicit a pathogenic effect (Knutton S, Lloyd D R, Candy D C, McNeish A S. In vitro adhesion of enterotoxigenic *Escherichia coli* to human intestinal epithelial cells from mucosal biopsies. *Infect Immun* 1984;44:514-8.) This means that the pathogen and/or its toxins can readily adhere to exposed eneterocytes and invade the host.

*Vibrio Cholerae* (Cholera)

*Vibrio cholerae* is a Gram-negative, facultative pathogen that is the causative agent of cholera, a devastating diarrheal disease that affects millions of people in the developing world each year; it survives in aqueous reservoirs, probably in the form of biofilms.

*Entamoeba Histolytica*

Invasive intestinal amebiasis, caused by *Entamoeba histolytica*, is initiated with attachment of trophozoites to the colonic mucous layer, mucous disruption and/or depletion, and adherence to and cytolysis of host epithelial and inflammatory cells. A current working model of intestinal amebiasis suggests that the microenvironment of the host intestine, particularly intestinal mucins and the bacterial biofilm, may influence the behavior of pathogenic amebae. Enzymes that disrupt bacterial biofilm will be useful in the inhibition and treatment of amebiasis.

All terms used herein, are used in accordance with their ordinary meanings unless the context or definition clearly indicates otherwise. Also unless expressly indicated otherwise, the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates, otherwise.

The scope of the present physiologically acceptable antibiofilm compositions, systems and methods, etc., includes both means plus function and step plus function concepts. However, claims are not to be interpreted as indicating a "means plus function" relationship unless the word "means" is specifically recited in a claim, and are to be interpreted as indicating a "means plus function" relationship where the word "means" is specifically recited in a claim. Similarly, claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion herein.

What is claimed is:

1. A method of inhibiting a biofilm infection in an internal surface of a mammal, said method comprising: orally administering to the mammal a therapeutically effective amount of a composition comprising a pharmaceutically acceptable carrier and enterically coated *Serratia* peptidase in combination with lactoferrin, an enzyme having dipeptidyl peptidase IV (DPP-IV) activity; chitosanase and an enzyme selected from the group consisting of papain, a lumbrokinase, and a nattokinase, for a time sufficient to cause significant biofilm degradation within the mammal wherein said internal surface of the mammal is selected from the group consisting of: heart, blood vessel, tendon, ligament, muscle, ureter, bladder, uterus, vagina, bone, gall bladder, pancreas, liver, and prostate.

2. The method according to claim 1 wherein the method further comprises administering an additional agent selected from the group consisting of a protease, and a peptidase, in an amount and for a time sufficient to cause significant biofilm degradation within the mammal.

3. The method according to claim 1 wherein the method further comprises administering an enzyme selected from the group consisting of ficin; kiwi protease; any plant-derived protease or proteinase, and phytase.

4. The method of any one of claim 1 wherein the method further comprises administering at least one of an acid-stable subtilisin and an acid-stable DNAse I in an amount and for a time sufficient to cause significant biofilm degradation within the mammal.

5. The method of any one of claim 1 wherein the method further comprises: further identifying the presence of at least one of *Borrellia* ssp, *Clostridium* ssp, *Klebsiella* ssp, *Pseudomonas* ssp, *Bacteroides* ssp, *Bacillus* ssp, *Yersinia* ssp, *Brucella* ssp, *Salmonella* ssp, *Shigella* ssp, *Fusobacterium* ssp, *Spirochaetes* ssp, *Entamoeba* ssp, *Candida* ssp, *Escherichia coli, Vibrio cholerae, Staphylococcus ssp, Streptococcus* ssp, *Hemophilus* ssp, *Aspergillus* ssp and *Gardnerella* ssp. in the mammal, and administering to the mammal a therapeutically effective amount of the anti-biofilm *Serratia* peptidase agent for a time sufficient to treat the identified *Borrellia* ssp, *Clostridium* ssp, *Klebsiella* ssp, *Pseudomonas* ssp, *Bacteroides* ssp, *Bacillus* ssp, *Yersinia* ssp, *Brucella* ssp, *Salmonella* ssp, *Shigella* ssp, *Fusobacterium* ssp, *Spirochaetes* ssp, *Entamoeba* ssp, *Candida* ssp, *Escherichia coli, Vibrio cholerae, Staphylococcus ssp, Streptococcus* ssp, *Hemophilus* ssp, *Aspergillus* ssp and *Gardnerella* ssp.

6. The method according to claim 1 wherein the method further comprises administering an antibiotic in an amount and for a time sufficient to cause significant biofilm degradation within the mammal.

7. The method according to claim 1 wherein the method further comprises administering a quercetin in conjunction with the *Serratia* peptidase, in an amount and for a time sufficient to cause significant biofilm degradation within the mammal.

8. The method according to claim 1 wherein the method further comprises administering seaprose in conjunction with the *Serratia* peptidase, in an amount and for a time sufficient to cause significant biofilm degradation within the mammal.

9. The method according to claim 1 wherein the method further comprises administering *Fusarium* protease in conjunction with the *Serratia* peptidase, in an amount and for a time sufficient to cause significant biofilm degradation within the mammal.

* * * * *